United States Patent [19]

Gygax

[11] Patent Number: 4,778,934
[45] Date of Patent: Oct. 18, 1988

[54] PROCESS FOR THE MANUFACTURE OF P-TERT-BUTYL-α-METHYLHYDROCIN-NAMALDEHYDE

[75] Inventor: Peter Gygax, Volketswil, Switzerland

[73] Assignee: Givaudan Corporation, Clifton, N.J.

[21] Appl. No.: 145,437

[22] Filed: Jan. 19, 1988

Related U.S. Application Data

[62] Division of Ser. No. 10,362, Feb. 3, 1987, Pat. No. 4,749,815.

[30] Foreign Application Priority Data

Feb. 14, 1986 [CH] Switzerland ............................ 598/86
Nov. 27, 1986 [CH] Switzerland .......................... 4742/86

[51] Int. Cl.$^4$ ........................................... C07C 43/166
[52] U.S. Cl. ..................................... 568/654; 568/630
[58] Field of Search ................................ 568/630, 654

[56] References Cited

U.S. PATENT DOCUMENTS 3,584,058  6/1971  Hahn ................................... 568/630
3,840,604  10/1974  Subroya et al. ...................... 568/654

FOREIGN PATENT DOCUMENTS 656060  1/1963  Canada .............................. 568/434
0036459  3/1980  Japan ................................ 568/434
0721401  3/1980  Japan ................................ 568/427

Primary Examiner—Werren B. Lone
Attorney, Agent, or Firm—Robert F. Tavares; Linda A. Vag

[57] ABSTRACT

A process for the manufacture of p-tert-butyl-α-methylhydrocinnamaldehyde which comprises the catalytic rearrangement of p-tert-butylbenzyl propenyl ether is provided.

2 Claims, No Drawings

PROCESS FOR THE MANUFACTURE OF P-TERT-BUTYL-α-METHYLHYDROCINNAMALDEHYDE

This application is a division of application Ser. No. 07/010,362 filed 02/03/87, now U.S. Pat. No. 4,749,815

THE INVENTION

The invention concerns a novel process for the manufacture of p-tert-butyl-α-methylhydrocinnamaldehyde, a known fragrance ingredient.

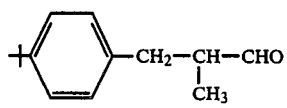

The process, as illustrated by Scheme I below, comprises a catalytic rearrangement of p-tert-butylbenzyl propenyl ether, II, to p-tert-butyl-α-methylhydrocinnamaldehyde, I. Ether II which may exist as the E- or Z-isomer or as a mixture of the two isomers, can be prepared by a catalytic isomerization of p-tert-butylbenzyl allyl ether, III. The allyl ether, III, can be prepared from p-tert-butylbenzyl chloride, IV, and allyl alcohol.

SCHEME I

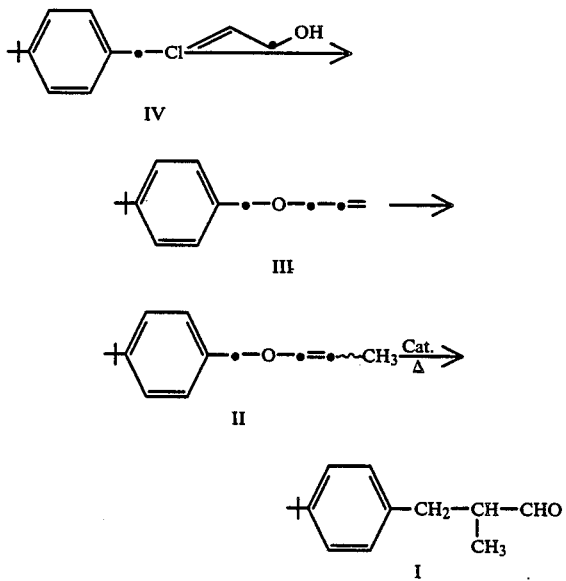

The ether intermediates, p-tert-butylbenzyl propenyl ether, II, and p-tert-butylbenzyl allyl ether, III, are novel compounds and form part of the present invention.

DESCRIPTION OF THE PREFERRED EMBODIMENTS

The catalytic rearrangement of p-tert-butylbenzyl propenyl ether, II, to p-tert-butyl-α-methylhydrocinnamaldehyde, I, is carried out in the presence of a copper halide, namely a copper(I) or copper(II) halide. It is preferred to use a copper(I) halide especially the iodide, bromide or chloride, in that order. Mixtures of copper-(I)/copper(II) halides in a ratio of from 1:100 to 100:1 can, however, also be effectively used. The halide may be either in the form of an anhydrous salt or a hydrated salt, i.e. containing water of crystallization. The anhydrous salts are preferred. The amount of halide to be used ranges from about 1 to about 20 wt.% of ether II. Amounts from about 2 to about 15 wt. % are preferred.

The rearrangement is carried out at elevated temperatures in a range from about 130° C. to about 300° C., preferably from about 135° C. to about 250° C. Temperatures of about 180° C. to about 200° C. are especially preferred.

The reaction is preferably conducted in the presence of a small amount of a base (e.g. about 1 to about 5 wt. %) although it is not necessary to do so. Especially suitable bases are carbonates and bicarbonates, particularly the alkali metal carbonates and alkali metal bicarbonates such as $Na_2CO_3$, $NaHCO_3$, etc.

Although the reaction is preferably carried out in the absence of a solvent, a solvent may be used if desired. Especially suitable solvents are high-boiling inert solvents such as paraffin oil, tert-butyltoluene, high-boiling ethers (e.g. diphenyl ether), etc. The amount of solvent used is not critical.

The reaction can be accelerated by the addition of a small amount (e.g. 0.5–2 wt. %) of an alkali iodide such as sodium iodide or potassium iodide.

It is also preferred to conduct the catalytic rearrangement under an inert atmosphere such as in an atmosphere of nitrogen.

The catalytic isomerization of p-tert-butylbenzyl allyl ether, III, to p-tert-butylbenzyl propenyl ether, II, can be carried out according to methods similar to those known for rearranging allylic ethers to vinyl ethers. (See e.g. Houben-Weyl, Methoden der organischen Chemie, Vol. 5/1b, (1972), pages 638–671.) Heterogeneous or homogeneous catalysts can be used for the isomerization, although heterogeneous catalysts are preferred. Table I lists the parameters suitable for both the heterogeneous and homogeneous catalyzed isomerization reactions.

TABLE I

| Heterogeneous catalysts (preferred) | | | |
|---|---|---|---|
| Noble metals, e.g. Ru, Pd, Rh, Pt; but also other metals, e.g. Ni, Co, Cu, Mo | Carrier; e.g. aluminium oxide, active carbon, silica gel | Temperature e.g. about 120–250° C., preferably about 140–200° C. | Solvent optional, especially high-boiling inert solvents such as hydrocarbons, ethers, aromatics |
| Homogeneous catalysts | | | |
| Noble metal (complex) compounds, e.g. tris-(triphenylphosphine)-ruthenium dichloride, bis-(triphenylphosphine)-rhodium | | About 100–150° C., preferably about 80–110° C. | Solvent optional, especially high-boiling inert solvents such as hydrocarbons, ethers, aromatics |

| TABLE I-continued | | |
|---|---|---|
| chloride | | |
| Iridium catalysts e.g. [Ir(cod)(PMePh$_2$)$_2$]-PF$_6$ (cod = cyclo-octadiene) | About 20° C. | Ethers, especially tetrahydrofuran |
| Metal carbonyls such as e.g. iron, molybdenum or tungsten carbonyls | About 50–200° C. | Solvent optional, especially high-boiling, inert solvents such as hydrocarbons, ethers, aromatics |

It is also preferred to conduct the catalytic isomerization under an inert atmosphere such as in an atmosphere of nitrogen.

The p-tert-butylbenzyl allyl ether, III, may be prepared from p-tert-butylbenzyl chloride, IV, and allyl alcohol by methods similar to those known for making benzyl allyl ethers, especially under the influence of bases. (See e.g. Houben-Weyl, *Methoden der organischem Chemie*, Volume 6/3, (1965), page 24 et seq.) The chloride IV and allyl alcohol are preferably reacted in a 1:1 stoichiometric ratio as this is the most economical reaction although an excess of allyl alcohol may also be used.

The reaction is preferably conducted in the presence of a base. Especially suitable bases are alkali metal hydroxides, alkaline earth metal hydroxides, alkali metal carbonates, alkaline earth metal carbonates, alkali metal bicarbonates, alkaline earth metal bicarbonates, etc. The base may be present in at least a stoichiometric amount although a moderate excess from about 10 to 50% may be used.

Although the reaction is preferably carried out in the absence of a solvent, a solvent may be used if desired. Suitable solvents are alkanes, aromatics and ethers.

The reaction may be carried out at temperatures between about 30° to 100° C., preferably between about 40° and 90° C. It is especially preferred to carry out the reaction at the optimal temperature range of about 60° to 70° C.

The reaction is preferably conducted in the presence of a phase transfer catalyst although it is not necessary to do so. As phase transfer catalysts there can be used, in particular, the usual tetrasubstituted ammonium salts. (See e.g. E.V. Dehmlow, Phase transfer catalysis, Verlag Chemie, (1983), page 104 et seq.) Crown ethers [see e.g. C.L. Liotta, *The Chemistry of Ethers* (Editor: S.Patai), Suppl. E, page 157 et seq.] are also very suitable, especially in the presence of alkali metal carbonates, e.g. sodium carbonate or potassium carbonate, in solvents such as acetone, whereby the reaction is carried out in an anhydrous system. (See e.g. M. Makosza et al., *J. Org. Chem.* Vol. 43, (1978), page 4682.)

ILLUSTRATION OF THE PREFERRED EMBODIMENTS

Example (a) 88 g (1.1 mol) of 50% sodium hydroxide solution are treated with 4.6 g (0.016 mol) of tetrabutylammonium chloride. At a temperature of 35° C. there is added dropwise within about 20 minutes while stirring well a mixture of 182.5 g (1.0 mol) of p-tert-butylbenzyl chloride and 61.5 g (1.06 mol) of allyl alcohol. The temperature is held at <70° C., which is accomplished if necessary by slight cooling. The mixture is stirred well at 70° C. for a further 12 hours. After cooling, the reaction mixture is washed twice with dilute hydrochloric acid. 204 g of practically pure p-tert-butylbenzyl allyl ether are obtained. The substance can be used without distillation for the next step.

B.p. of the distilled material: about 90° (0.1 Torr).

(b) 204 g (1.0 mol) of p-tert-butylbenzyl allyl ether are treated with 2.04 g of ruthenium on aluminium oxide (5%) and stirred under a nitrogen atmosphere for 1 hour at a bath temperature of 180° C. After filtering off the catalyst the remainder is distilled in a high vacuum. There are obtained 163.4 g of p-tert-butylbenzyl propenyl ether as a mixture of the Z- and the E-isomers (80.1% of theory based on p-tert-butylbenzyl chloride).

B.p.: 140°–145° C.

(c) 15.3 g of copper$^{1+}$iodide, 2.55 g of sodium carbonate and 1.02 g of sodium iodide are placed at 185° C. under nitrogen in a flask with a dropping funnel, a thermometer and a stirrer. 101.8 g (0.49 mol) of p-tert-butylbenzyl propenyl ether (isomer mixture) are added dropwise within 13 minutes. After stirring at 185°–190° C. for a further 10 minutes the heating is removed and, after cooling the reaction mixture, the catalyst is separated by filtration. Distillation in a high vacuum gives 69.4 g (68.2% of theory) of pure p-tert-butyl-α-methylhydrocinnamaldehyde, b.p. 110° C.

Analogous results can be obtained for reaction (c), above, when the following are substituted:
a mixture of Cu$^{1+}$/Cu$^{2+}$bromide (1:1),
a mixture of Cu$^{1+}$/Cu$^{2+}$chloride (1:1),
CuBr,
CuCl,
CuBr$_2$,
CuCl$_2$,
by carrying out the reaction in paraffin oil (boiling point >200° C.),
by carrying out the reaction at 160° or at 200° C., or by halving the amount by weight of catalyst.

We claim:
1. p-tert-Butylbenzyl allyl ether.
2. p-tert-Butylbenzyl propenyl ether.

* * * * *